United States Patent [19]

Silber

[11] Patent Number: 4,786,284

[45] Date of Patent: Nov. 22, 1988

[54] DISCONNECTIBLE SECTION OSTOMY APPLIANCE

[76] Inventor: Arthur L. Silber, 543 Dobbins Dr., San Gabriel, Calif. 91775

[21] Appl. No.: 835,782

[22] Filed: Mar. 3, 1986

[51] Int. Cl.⁴ ............................................. A61F 5/44
[52] U.S. Cl. ................................... 604/342; 604/339
[58] Field of Search ..................... 604/327, 332–345; 4/144.1–144.4

[56] References Cited

U.S. PATENT DOCUMENTS

| | | | |
|---|---|---|---|
| 2,002,931 | 12/1931 | Bowman | 604/345 |
| 2,834,347 | 5/1958 | Connally. | |
| 3,081,771 | 3/1963 | Lee | 604/344 |
| 3,163,162 | 12/1964 | Basseches. | |
| 3,495,592 | 2/1970 | Herman | 604/338 |
| 3,528,420 | 9/1970 | Nielsen | 604/342 |
| 3,612,053 | 10/1971 | Pratt | 604/338 |
| 3,941,133 | 3/1976 | Chen | 604/344 |
| 4,518,389 | 5/1985 | Steer et al. | 604/339 |
| 4,526,166 | 7/1985 | Silber. | |
| 4,559,048 | 12/1985 | Steer | 604/339 |

FOREIGN PATENT DOCUMENTS 0372770 3/1973 U.S.S.R. .............................. 604/344

Primary Examiner—John D. Yasko
Assistant Examiner—Mario Costantino
Attorney, Agent, or Firm—William W. Haefliger

[57] ABSTRACT

A disconnectible section ostomy appliance comprises
(a) a receptacle for body waste discharge,
(b) a first support strip connected to said receptacle,
(c) a second support strip carrying an adhesive adapted to be pressed onto an area proximate an ostomy orifice in the body for passing said body discharge,
(d) and a releasable attachment interconnecting said first and second strips, so that the receptacle is positioned to receive waste discharge from said ostomy orifice, the attachment adapted to be manually manipulated to free the connection between said strips, whereby the first strip and receptacle are liftable away from the skin without restriction imposed by said adhesive.

9 Claims, 1 Drawing Sheet ction ostomy
DISCONNECTIBLE SECTION OSTOMY APPLIANCE

BACKGROUND OF THE INVENTION

This invention relates generally to ostomy appliances, and more particularly to easily releasable attachment of waste receiving receptacles to ostomy patients' skin areas.

Present day ostomy receptacles are highly useful; however, they are frequently difficult to remove without creating discomfort and irritation at the site of attachment. This difficulty results from the fact that force is required to free the receptacle from the necessarily strong adhesive bond to the body wall, and tends to substantially stretch and chronically irritate the skin around the stoma site. Also waste spillage can occur during such forceful removal process.

SUMMARY OF THE INVENTION

It is a major object of the invention to provide an improved ostomy appliance overcoming the above described disadvantages and problems, as well as others, as will appear. The appliance typically comprises:

(a) a receptacle for body waste discharge, (b) a first support strip connected to said receptacle, (c) a second support strip carrying an adhesive adapted to be pressed onto an area proximate an ostomy orifice in the body for passing said body discharge, (d) and a releasable attachment interconnecting said first and second strips, so that the receptacle is positioned to receive waste discharge from said ostomy orifice, the attachment adapted to be manually manipulated to free the connection between said strips, whereby the first strip and receptacle are liftable away from the skin without restriction imposed by said adhesive.

The described attachment may advantageously comprise a stitching interconnecting the strips, the stitching preferably being in the form of a string freed from the strips by endwise pull. Other attachments performing the ready-release function are also usable.

Also, the first strip typically extends peripherally of said second strip, said second strip defining a through opening to pass the waste discharge from said orifice to the receptacle; and the stitching may extend peripherally about the second strip, spaced from the through opening in the latter. The first strip is typically annular to surround the second strip, whereby the receptacle, which is flat, may lie adjacent the second strip, preventing leakage of waste therebetween. If desired, a waste guiding tongue may extend into the receptacle from the second strip.

Finally, the invention enables use of a sequence of such replacement appliances, the second strip of each being adhesively attachable, by finger pressure, onto the second strip of the previously used appliance, as will appear.

These and other objects and advantages of the invention, as well as the details of an illustrative embodiment, will be more fully understood from the following specification and drawings, in which:

DRAWING DESCRIPTION

DETAILED DESCRIPTION

Figure 1:
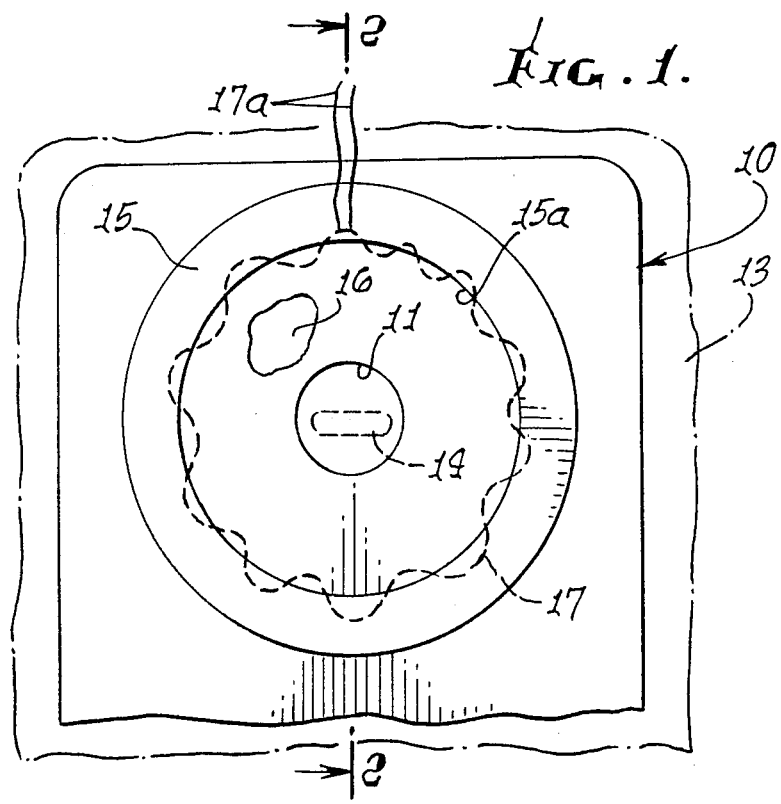
FIG. 1 is a side elevation showing the construction of the appliance.
Figures 2, 2A:
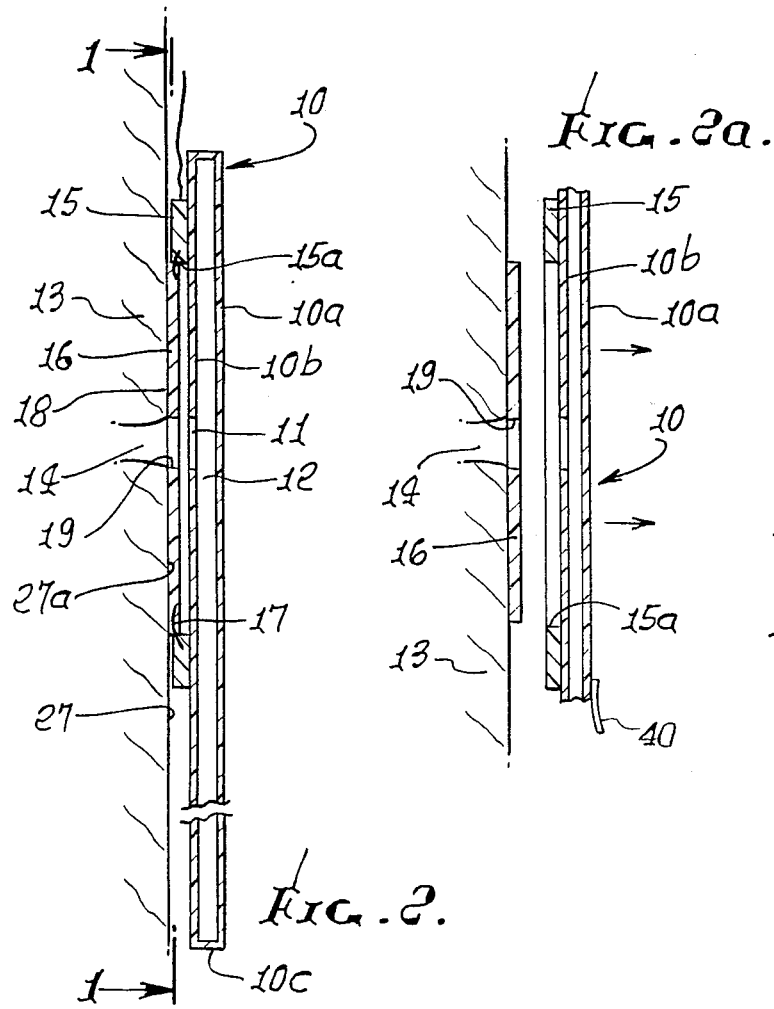
FIG. 2 is a section on lines on 2—2 of FIG. 1.
FIG. 2a is a view like FIG. 2, but showing removal of ostomy receptacle and attached first strip, away from the second strip adhesively attached to skin area around the stoma.

In FIGS. 1 and 2, a flat receptacle for body waste discharge is indicated at 10, and includes an outer plastic (or other material) sheet 10a, an inner sheet 10b, and a peripheral interconnection 10c, for the sheet. The sheet 10b defines a through opening 11 to pass waste into the receptacle (see arrow 12 that discharges from the patient's or user's body 13, via an ostomy orifice (stoma) 14.

A first support strip 15 is suitably connected to the receptacle, as by suitably strong adhesive joining it to inner sheet 10b, or elements 15 and 10b may be integral or unitary. Strip 15 may consist of plastic or other material, and extends in bounding relation about an enlarged opening, defined by the inner boundary 15a of strip 15. Boundary 15a may be circular, or generally circular, (elliptical, round cornered, etc.). Boundary 15a also extends about and is spaced from side opening 11 in sheet 10b.

A second sheet support strip 16 is attached to the skin area 17 of the body 13, about or proximate the orifice 14. Such attachment may be via adhesive 18 carried by the strip 16, at its inner side. This adhesive may be made less irritating to skin than the stronger adhesive used on devices placed over 16 on further devices (next day etc.). The strip 16 may define a through opening 19 in registration with and adjacent the orifice 14, to directly pass waste to the receptacle entrance 11. The receptacle and first strip may have a tab 40 for holding onto during the removal from the adherent strip. See FIG. 2a.

As will appear, the invention enables non-removal or pull-off of the strip 16 (with concomitant avoidance of painful pull of the adhesive on the skin area 17), during changing of the receptacle 10.

A releasable attachment interconnects the first and second strips so that the receptacle 10 is retained to the body 13, and positioned to receive waste discharge from orifice 14. In this regard, the attachment is such as to be readily and easily manually manipulated to free the connection between the strips, whereby the first strip and receptacle are then liftable (as by tab 40) away from the skin without restriction imposed by the adhesive. As will appear, a replacement receptacle and associated first and second strips can then be positioned adjacent the second strip that is attached to the skin 27, and the replacement second strip easily and quickly adhesively attaches to said second strip attached to the skin, to complete the attachment of the replacement receptacle to the body, and in such manner as to enable easy and quick removal of the replacement receptacle and without pull on the skin area 27a.

As shown, the attachment may with unusual advantage take the form of stitching interconnecting the strips 15 and 16, and in particular the stitching appears as a string or thread 17 undulating in wave form between the strips. One or both ends 17a of the string projects or project to the exterior, i.e. free of the appliance, to be pulled so as to pull the entire string or thread endwise, freeing it from the strips, and disconnecting them. The receptacle and strip 15 may then be lifted free of strip 16 (see FIG. 2a), the latter remaining adhesively attached to the body. Both ends may be free of the appliance, but secured prior to pulling purposefully, so that accidental separation of first strip and receptacle cannot occur.

Strip 15 typically extends peripherally of strip 16, and strip 16 may be circular as shown, or non-circular (elliptical, round-cornered, etc.).

Figure 4:
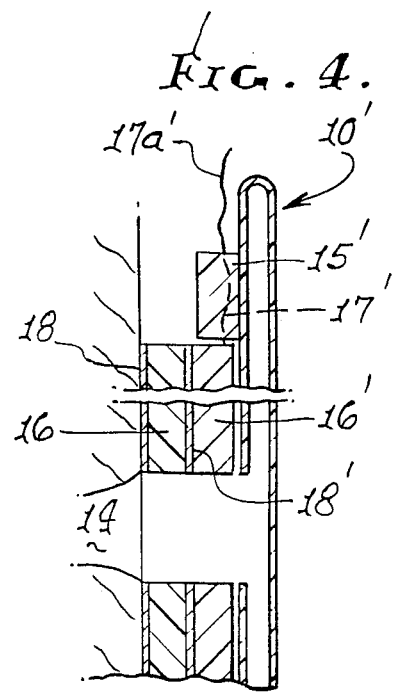
FIG. 4 is an enlarged fragmentary section showing a further modification.

FIG. 4 shows a "second" strip 16 directly attached to the body 13, via adhesive 18; and a replacement "second" strip 16' attached via adhesive 18' to strip 16. Strip 16' is attached via stitching 17' to replacement first strip 15', which is in turn integral with replacement receptacle 10'. Strip 16 may be considered as a third strip.

Figure 3:
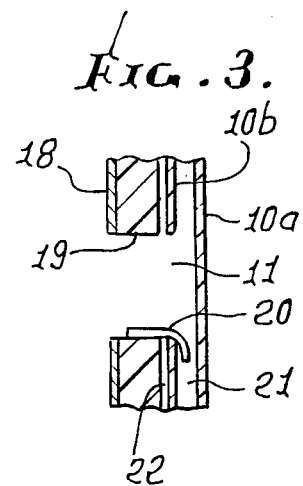
FIG. 3 is an enlarged fragmentary section, showing a modification.

In FIG. 3, a waste guiding tongue 20 extends from the boundary of opening 19, (with which it is integral) through opening 11, and overhangs wall 10b of the receptacle as it extends into the receptacle interior 21. This construction prevents spillage of waste into the space 22 between wall 10b and strip 16, during waste discharge into the receptacle.

I claim:

1. In a disconnectible section ostomy appliance, the combination comprising:
   (a) a receptacle for body waste discharge, said receptacle having air inlet for receiving body waste discharge
   (b) a first support strip connected to said receptacle,
   (c) a second support strip carrying an adhesive wherein the strip can be pressed and adhered to the body for passing said body discharge,
   (d) and a releasable attachment interconnecting said first and second strips, so that the receptacle is positioned to receive waste discharge from said ostomy orifice, the attachment being manually to free the connection between said strips, whereby the first strip and receptacle are liftable away from the skin without restriction imposed by said adhesive,
   (e) said attachment comprising stitching interconnecting said strips.

2. The combination of claim 1 wherein the stitching comprises string means releasably threaded between the strips, the string means having two free ends, wherein when one end is pulled the string means is removed from the strips.

3. The combination of claim 1 wherein said second strip has a perimeter and said first strip extends peripherally of said second strip perimeter, said second strip defining a through opening to pass the waste discharge from said orifice to the inlet of the receptacle.

4. The combination of claim 3 wherein the receptacle entrance is in registration with said second strip through opening.

5. The combination of claim 1 wherein the second strip includes a waste guiding tongue extending into said receptacle entrance and overlapping a portion of said stitching.

6. The combination of claim 1 wherein said second strip has a perimeter and said first strip is generally annular and entends peripherally of said second strip perimeter.

7. The combination of claim 1 including a third strip carrying an adhesive wherein the strip can be pressed and adhered to a skin area proximate said ostomy orifice, the said second strip adhesively attached to said third strip.

8. The combination of claim 7 wherein said second and third strips define through openings which are in registration to pass the waste discharge from said orifice to the receptacle.

9. In a disconnectible section ostomy appliance, the combination comprising:
   (a) a receptacle for body waste discharge,
   (b) a first support strip connected to said receptacle,
   (c) a second support strip carrying an adhesive which can be pressed onto an area proximate an ostomy orifice in the body for passing said body discharge,
   (d) and a releasable attachment interconnecting said first and second strips, so that the receptacle is positioned to receive waste discharge from said ostomy orifice, the attachment being manually manipulatable to free the connection between said strips, whereby the first strip and receptacle are liftable away from the skin without restriction imposed by said adhesive,
   (e) said second strip having a perimeter and said first strip extending peripherally of said second strip perimeter, said second strip defining a through opening to pass the waste discharge from said orifice to the receptacle,
   (f) the receptacle having an entrance in registration with said second strip through opening,
   (g) said attachment comprising stitching extending peripherally about said second strip and interconnecting the strips, and spaced from said opening.

* * * * *

UNITED STATES PATENT AND TRADEMARK OFFICE
CERTIFICATE OF CORRECTION

PATENT NO. : 4,786,284

DATED : November 22, 1988

INVENTOR(S) : Arthur L. Silber

It is certified that error appears in the above-identified patent and that said Letters Patent is hereby corrected as shown below:

Column 3, line 35; "ostomy orifice, the attachment being manually to" should read --ostomy orifice, the attachment being manually manipulatable to --.

Signed and Sealed this

Eighteenth Day of July, 1989

Attest:

DONALD J. QUIGG

Attesting Officer

Commissioner of Patents and Trademarks